April 8, 1975 T. YUGE Plant Pat. 3,701
AZALEA PLANT
Filed April 10, 1974
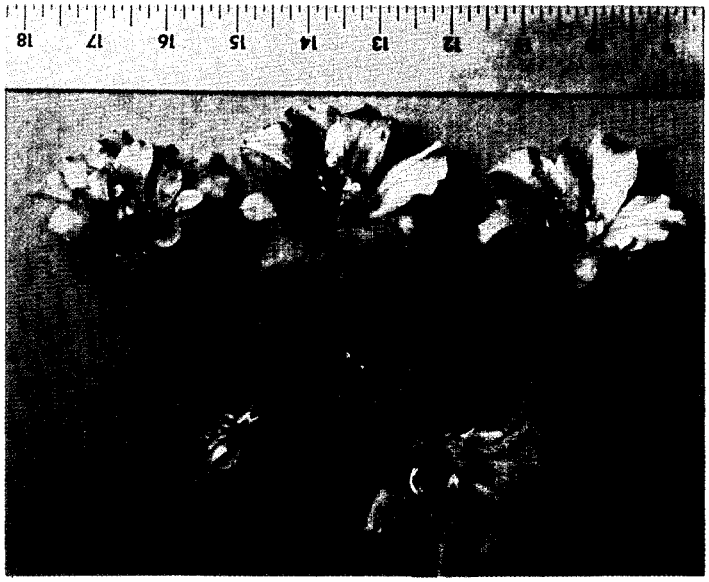
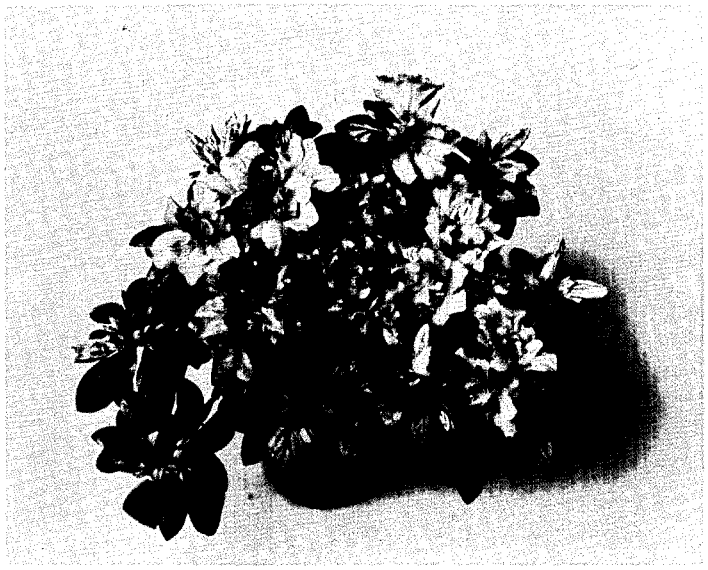
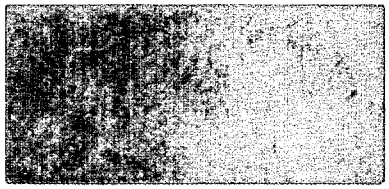

United States Patent

Plant Pat. 3,701

Patented Apr. 8, 1975

3,701

AZALEA PLANT

Takeo Yuge, Altadena, Calif., assignor to Geo. J. Ball, Inc., Chicago, Ill.

Filed Apr. 10, 1974, Ser. No. 459,657

Int. Cl. A01h *5/00*

U.S. Cl. Plt.—57 1 Claim

ABSTRACT OF THE DISCLOSURE

A new variety of azalea plant particularly adapted for greenhouse pot-forcing and distinguished by its profuse production of rose red blossoms and its compact, profusely branched growth habit.

BACKGROUND OF THE INVENTION

This new variety of azalea plant originated as a seedling of Chimes (unpatented) × Red Hot (P.P. 3,155) crossed by me in the course of extensive breeding efforts carried on by me at Altadena, Calif., with the object of developing improved varieties of azalea plants adapted for greenhouse pot-forcing and especially suitable for the commercial trade. This new plant was observed by me in 1969 to have a profuse production of attractive red blossoms of medium size which completely covered a compact, much branched growth of dark green foliage and because a plant with these characteristics is considered to be especially choice in the commercial market, this plant was selected by me for propagation and testing.

Subsequent asexual propagation of this plant, by means of vegetative cuttings, under my direction at Altadena, Calif., has shown that its distinctive and desirable characteristics hold true from generation to generation and thus appear to be firmly fixed. Consequently this new azalea variety is now being propagated on a commercial scale, by vegetative cuttings, at Salem, Oreg., Woodburn, Oreg., and San Fernando, Calif.

DESCRIPTION OF THE DRAWING

This new variety of azalea plant is illustrated by the accompanying photographic drawing, in full color, which shows a blooming potted plant in the lower view and a close-up showing of buds and blossoms in the upper view, the colors shown being as nearly true as can be reasonably obtained by conventional photographic procedures. The color patch mounted below the lower view shows the true flower color.

DESCRIPTION OF THE NEW PLANT

The following is a detailed description of my new azalea plant with color designations according to the Horticultural Colour Chart produced by Robert F. Wilson and published by the British Colour Council in collaboration with The Royal Horticultural Society of London, England.

The plant

Origin: Seedling.
Parentage:
- *Seed parent*—Chimes (unpatented).
- *Pollen parent*—Red Hot (P.P. 3,155).

Classification:
- *Botanic.*—Rhododendron.
- *Commercial.*—Hybrid azalea, pot-forcing type.

Form: Bush—as a potted plant.
Height: Medium.
Growth: Vigorous, upright and sturdy, but limber.
Branching: Profusely branched, but compact.
Foliage: Quantity—abundant.
- *Leaf shape.*—Generally elliptic, with acute apiculate apex and attenuate or acuminate base.
- *Leaf size.*—Variable, from about 1⅛ to 2⅜ inches long.

- *Texture.*—Leathery, rough and puberulent.
- *Aspect.*—Glossy.
- *Ribs and veins.*—Netted.
- *Color.*—Upper side—Ivy Green 0001060/2. Under side—Spinach Green 0960/1.

Petioles: ¼ to ⅜ inch long.

The bud

Form: Elliptical and pointed.
Size: Small to medium, 1 inch long, ⅜ to ½ inch in diameter.
Opening: The bud opens slowly.
Color:
- *When sepals first divide.*—Spirea Red 025.
- *When petals unfurl.*—Spirea Red 025.

Sepals: Very irregular and tomentose, partly metamorphosed to be petal-like.
Color:
- *Inside.*—Rose Red 724/2 with irregular white to Pea Green 61/1 streaks.
- *Outside.*—Rose Red 724/3 with irregular white to Pea Green 61/2 streaks.

Calyx: Long, funnel-shaped, petal-like and irregular.
- *Aspect.*—Hairy.

Peduncle: Erect, ¼ to ⅜ inch long.
- *Aspect.*—Hairy, with silvery hairs.
- *Color.*—Fern Green 0862/1. Some tinged with Chrysanthemum Crimson 824.

The flower

Blooming habit: Recurrent. Blooming profusely once in mid-season to late spring. Has a tendency to give a few blossoms in summer and fall.
Size: Medium. 2½ to 2¾ inches in diameter and 1¼ to 1½ inches in depth.
Borne: In clusters.
Shape: When blossom first opens—Funnel or trumpet shaped. Form changes to be more broad and flat as the blossom matures.
Petalage: Number of petals—6 to 8, fused at base.
- *Arrangement.*—Semi-double, hose-in-hose and connate.
- *Form.*—Ovate with undulate margins.
- *Color.*—Outer petals—Rose Red 724 in body with freckling of Garnet Lake 828/1 at base of standard and upper wings. Inside petals—Rose Red 724/1. Reverse side—Spirea Red 025.
- *Texture.*—Soft.
- *Appearance.*—Satiny.
- *Discoloration (after full bloom).*—Slight.

Petaloids: Number—23 to 25 fused.
- *Size.*—1 to 1¼ inches long.
- *Color.*—Rose Red 724/2.

Peduncle: Sturdy and upright and tomentose. ¼ to ⅜ inch long.
- *Color.*—Chrysanthemum Crimson 824/3 shading to Pod Green 061 at base.

Persistence: Petals hang on and dry.
Fragrance: None.
Disease resistance: Plant resists all diseases prevalent in the area where it is being grown.
Lasting quality: Very good on plant.

Reproductive organs

Stamens: Anthers—Basifixed on filament. Number—8 to 12. Length—⅛ inch.
- *Filaments.*—Length ¾ to 1 inch, some fused to petaloids. Color—Camellia Rose 622.
- *Pollen.*—None observed.

Pistils: Number—One. Length—1 to 1¼ inches.
- *Stigmas.*—Color—Geranium Lake 20/2.

Ovaries: Superior, wall very hirsute.

This new azalea variety most closely resembles the variety Red Hot (P.P. 3,155) and is distinguished in particular by the considerably smaller size of its profusely produced blossoms which more fully cover the crown of its very compact plant growth. As a potted plant of medium height, this new variety, while having almost the same coloration as Red Hot, has the advantage of blossom mass which finds favor in the retail market of the florist trade.

I claim:

1. A new and distinct variety of azalea plant substantially as herein shown and described, characterized by its compact and much branched growth habit and its profuse production of deep red blossoms of medium size.

No references cited.

ROBERT E. BAGWILL, Primary Examiner